United States Patent [19]

Yokozeki et al.

[11] Patent Number: 4,666,838

[45] Date of Patent: May 19, 1987

[54] PROCESS FOR THE PRODUCTION OF L-ASPARTYL-L-PHENYLALANINE ESTERS

[75] Inventors: Kenzo Yokozeki; Eiji Majima, both of Kawasaki; Yoshiteru Hirose, Kamakura; Takeru Sato, Kawasaki; Toshihide Yukawa, Yokohama, all of Japan

[73] Assignee: Ajinomoto Co., Inc., Tokyo, Japan

[21] Appl. No.: 707,808

[22] Filed: Mar. 4, 1985

[30] Foreign Application Priority Data

Mar. 7, 1984 [JP] Japan ................................. 59-43489
Jul. 27, 1984 [JP] Japan ............................... 59-156686

[51] Int. Cl.$^4$ ...................... C12P 21/02; C12N 1/20; C12N 1/14; C12N 1/18

[52] U.S. Cl. ..................................... 435/70; 435/253; 435/254; 435/255; 435/256

[58] Field of Search .................. 435/70, 68, 253, 183, 435/191, 225, 232, 254, 255, 256; 426/548

[56] References Cited

U.S. PATENT DOCUMENTS 4,587,214  5/1986  Harada et al. ......................... 435/68

FOREIGN PATENT DOCUMENTS 0074095  3/1983  European Pat. Off. .............. 435/70

OTHER PUBLICATIONS

Snoke, "On the Mechanism of the Enzymatic Synthesis of Glutathione", J.A.C.S. 75 pp. 4872-4873 (1953).
Ito et al., "Enzymatic Synthesis of the Peptide in Bacterial Uridine Nucleotides", Journal of Biological Chemistry 237 (8), pp. 2689-2695 (1962).

Primary Examiner—Charles F. Warren
Assistant Examiner—John E. Tarcza
Attorney, Agent, or Firm—Oblon, Fisher, Spivak, McClelland, & Maier

[57] ABSTRACT

A process for producing L-aspartyl-L-phenylalanine alkyl or aryl esters wherein L-aspartic acid and L-phenylalanine which is esterified with an alkyl group having at least two carbon atoms, an aryl group or an aralkyl group, are contacted in an aqueous medium with particular microorganisms or enzyme fractions from these microorganisms and the condensed product crystallizes out due to insolubility in the aqueous medium.

22 Claims, No Drawings

PROCESS FOR THE PRODUCTION OF L-ASPARTYL-L-PHENYLALANINE ESTERS

BACKGROUND OF THE INVENTION

1. Field of the Invention

This invention relates to a process for producing L-aspartyl-L-phenylalanine alkyl, aryl or aralkyl esters.

2. Description of the Prior Art

L-aspartyl-L-phenylalanine esters are peptides which have been noted as sweeteners in recent years. L-aspartyl-L-phenylalanine methyl ester (abbreviated as APM hereinafter) is a well known example of such a sweetener.

It is well known that the process for production of APM includes both chemical and enzymatic synthetic processes.

The chemical synthetic process for the production of APM comprises condensing N-protected L-aspartic acid anhydride and L-phenylalanine methyl ester (abbreviated as PM hereinafter) to obtain N-protected APM from which the protective group is subsequently removed. The enzymatic synthetic process comprises allowing a protein-decomposing enzyme to act on an N-protected L-aspartic acid and PM to obtain N-protected APM, or the PM adduct of N-protected APM, and then removing the protective group to form APM. However, both processes require the complicated steps of introducing and removing protective groups.

A process is also known for producing APM without using protective groups (see Japanese Patent Kokai No. 126796/1983, "Digests of the Publications at the Annual Meeting of the Agricultural Chemical Society of Japan" in 1983, p. 42). This process is a microbiological synthetic process which uses a microorganism selected from one of the following genuses: Pseudomonas, Torulopsis, Rhodotorula, and Sporobolomyces. This process, however, is not always suitable for the industrial production of APM because it produces extremely low yields.

The present inventors have previously found that by employing microorganisms, one can bring about the direct and effective formation of APM from L-aspartic acid and PM (see Japanese Patent Application No. 75559/1983).

However, a major drawback associated with processes for producing aspartyl-phenylalanine esters using as a starting material unprotected L-aspartic acid is the fact that the reaction forming APM from L-aspartic acid and PM is an equilibrium reaction, and this equilibrium prevents the substrates from being converted efficiently to aspartyl-phenylalanine ester products.

Therefore, a need continues to exist for a process providing for the efficient conversion of unprotected L-aspartic acid in reaction with L-phenylalanine esters to produce L-aspartyl-L-phenylalanine ester products in good yields.

SUMMARY OF THE INVENTION

Accordingly, it is an object of the present invention to provide a process for the production of L-aspartyl-L-phenylalanyl esters in good yields.

It is another object of the present invention to provide a process for the microbial production of L-aspartyl-L-phenylalanyl esters in good yields.

It is another object of the present invention to provide a process for the microbial extract or enzymatic production of L-aspartyl-L-phenylalanine esters in good yields.

It is another object of the present invention to provide a process for the production of L-aspartyl-L-phenylalanyl esters in good yields, where an unprotected L-aspartic acid starting material is used.

It is another object of the present invention to provide a process for the production of L-aspartyl-L-phenylalanyl esters, where a L-phenylalanine ester starting material is used.

It is another object of the present invention to provide a process for the production of L-aspartyl-L-phenylalanyl esters, where the product formed has a low solubility in the reaction medium.

These and other objects of the present invention have been realized by contacting an unprotected L-aspartic acid and a L-phenylalanine ester with a microorganism or an enzyme-containing fraction of the microorganism.

The L-phenylalanine ester used in accordance with the present invention comprises L-phenylalanine esterified with a moiety containing at least 2 carbon atoms. The esterifying moiety may be a straight, branched or cyclic alkyl group containing at least 2 carbon atoms. The esterifying moiety may also be an unsubstituted or substituted aryl group containing at least 5 carbon atoms, or an unsubstituted or substituted aralkyl group containing at least 6 carbon atoms.

DESCRIPTION OF THE PREFERRED EMBODIMENTS

The abbreviation PR is used in this application to represent phenylalanine esterified with alkyl, aryl or aralkyl alcohols where the alkyl moiety has two or more carbon atoms. The substituents on the aryl group are not specifically limited but, for example, may include one or more halogens, alkyl groups of 1–10 carbon atoms, nitro groups and cyano groups.

Furthermore, the L-phenylalanine ester or the L-aspartic acid may be in the form of free bases or salts of any of various acids, such as, for example, hydrochloric acid, p-toluenesulfonic acid, trifluoroacetatic acid, hydrobromic acid, formic acid or acetic acid.

APR itself is expected not only to be used as a sweetener but also to be used as a raw material to synthesize APM by ester exchange or any other method.

Accordingly, this invention is directed to a process for the production of APR, characterized by contacting L-aspartic acid and PR with at least one microorganism selected from one of the following genuses: Corynebacterium, Candida, Cryptococcus, Escherichia, Flavobacterium, Geotrichum, Micrococcus, Pachysolen, Saccharomyces, Trichosporon, Xanthomonas, Kluyveromyces, Endomyces, Arthrobacter, Cellulomonas and Brevibacterium.

The process for converting L-aspartic acid and PR to APR by conducting the condensation in an aqueous medium through the action of microorganisms selected from the above-mentioned genuses can be carried out by contacting L-aspartic acid and PR with microorganism cells, culture solutions or microorganism cell-treating materials of the above-mentioned microorganisms.

The following are examples of the microorganisms which have the ability to convert L-aspartic acid and PR to APR by condensation in this invention:

*Corynebacterium sp.:* ATCC 21251
*Corynebacterium xerosis:* ATCC 373

*Candida intermedia:* FERM-BP508
*Cryptococcus neoformans:* IFO 4289
*Escherichia coli:* FERM-BP477
*Flavobacterium sewanens:* FERM-BP476
*Geotrichum candidum:* IFO 4599
*Micrococcus luteus:* ATCC 4698
*Pachysolen tannophilus:* IFO 1007
*Trichosporon capitatum:* IFO 1197
*Xanthomonas campestris:* FERM-BP507
*Kluyveromyces thermotolerans:* IFO 0662
*Endomyces ovetencis:* IFO 1201
*Saccharomyces cerevisiae:* IFO 2003
*Arthrobacter citreus:* ATCC 11624
*Cellulomonas flavigena:* ATCC 8183
*Brevibacterium linens:* ATCC 8377

The cells of these microorganisms can be obtained by using ordinary culture media.

L-aspartic acid and PR may be added at the beginning or in the process of cultivation of these microorganisms.

The culture media to be used for the microorganisms of this invention are ordinary ones containing usual carbon and nitrogen sources and inorganic ions in addition to L-aspartic acid and PR. Moreover, the addition of trace amounts of organic nutritive substances such as vitamins and amino acids often brings about desirable results.

The carbon sources suitable for use in this invention include carbohydrates such as glucose and sucrose, organic acids such as acetic acid, alcohols and the like. The nitrogen sources suitable for use herein include ammonia gas, aqueous ammonia, ammonium salts, and the like. The inorganic ions may be magnesium ion, phosphoric acid ion, potassium ion, iron ion, and the like.

The cultures are conducted under aerobic conditions at pH 4-8 at suitable temperatures controlled within the range of 25°-40° C., and for 1-10 days to obtain desirable results.

The microorganisms to be used in this invention include the whole culture solutions obtained after completion of the cultivation thereof, the microorganisms separated from the culture solutions, or washed microorganisms. Also, the microorganisms to be used in this invention may be freeze-dried, acetone-dried, contacted with toluene, surfactants, etc., treated with lysozyme, exposed to ultrasonic waves, mechanically ground or treated in any manner which results in obtaining an enzyme protein fraction having enzyme activity which can change L-aspartic acid and PR to APR. The fixed cells of these microorganisms, insolubilized materials obtained from cell-treating materials, etc. may be used.

As aqueous media, there can be used those containing water, buffers, and organic solvents such as ethanol. Moreover, nutritive elements needed for the growth of microorganisms, anti-oxidants, surfactants, coenzymes, hydroxylamine and metallic ions, etc. can be added to the aqueous media if necessary.

When the cells of the above-mentioned microorganisms are grown in aqueous media and simultaneously contacted with L-aspartic acid and PR so as to exert action thereon, the aqueous media should contain L-aspartic acid, PR, and nutritive elements such as carbon sources, nitrogen sources, and inorganic ions, etc. needed for the growth of microorganisms as described above. Further, the addition of trace amount of organic nutritive elements such as vitamins and amino acids often brings about desirable results.

When the whole culture solutions, culture cells or cell-treating materials of the above-mentioned microorganisms are contacted with L-aspartic acid and PR to exert action thereon, the aqueous media are prepared by dissolving or suspending L-aspartic acid, PR and the culture solutions, microorganism culture cells, or microorganism cell-treating materials. The media are then maintained at proper temperatures of 10°-70° C., at a pH of 4-8, and are allowed to stand or are stirred. As a result, a great deal of APR is produced and accumulated in the aqueous media after 5-100 hours.

The APR thus produced can be separated and purified by known processes for separation. The APR obtained may be characterized with an amino-acid analyzer.

The invention now being generally described, the same will be better understood by reference to certain specific examples which are included herein for purposes of illustration only and are not intended to be limiting of the invention or any embodiment thereof.

EXAMPLE 1

Into a 500 ml flask was introduced 50 ml of a medium (pH 7.0) containing 2.0 g/dl of glucose, 0.5 g/dl of $(NH_4)_2SO_4$, 0.1 g/dl of $KH_2PO_4$, 0.1 g/dl of $K_2HPO_4$, 0.1 g/dl of $MgSO_4.7H_2O$, 0.05 g/dl of $FeSO_4.7H_2O$, 1 mg/dl of $MnSO_4.4H_2O$, 1.0 mg/dl of yeast extract, 0.5 g/dl of malt extract, and 4.0 g/dl of calcium carbonate, which was sterilized at 120° C. for 15 minutes.

Each one of the thus prepared media was inoculated, using a platinum loop with *Flavobacterium sewanens* FERM-BP476 or *Arthrobacter citreus* ATCC 11624, incubated in a bouillon-agar medium at 30° C. for 24 hours, and cultured at 30° C. for an additional 20 hours. The cells were harvested from this culture solution by centrifugation, washed once with the same amount of physiological saline as that of the culture solution and collected.

These microorganism cells were added to Reaction Solution A shown in Table 1 to equal 5 g/dl (final conditions, pH 5.4, 5 ml), and allowed to react at 37° C. for 16 hours. The resulting APR was determined with an amino acid analyzer to give the results in Table 2.

TABLE 1

| Reaction Solution A* | |
|---|---|
| L-aspartic acid | 10 g/dl |
| L-phenylalanine ester or its hydrochloride shown in Table 2 | 15 g/dl |

*The substrates are included in 0.1 M phosphoric acid buffer (final pH 5.4).

TABLE 2

| | APR formed (mg/dl) | |
|---|---|---|
| Phenylalanine ester or its hydrochloride starting material | *Flavobacterium sewanens* FERM-BP476 | *Arthrobacter citreus* ATCC 11624 |
| Phenylalanine methyl ester hydrochloride | 590 | 583 |
| Phenylalanine ethyl ester hyorochloride | 710 | 702 |
| Phenylalanine n-propyl ester hydrochloride | 812 | 810 |

TABLE 2-continued

| Phenylalanine ester or its hydrochloride starting material | APR formed (mg/dl) | |
|---|---|---|
| | Flavobacterium sewanens FERM-BP476 | Arthrobacter citreus ATCC 11624 |
| Phenylalanine iso-propyl ester hydrochloride | 1020 | 1005 |
| Phenylalanine n-butyl ester hydrochloride | 920 | 911 |
| Phenylalanine isobutyl ester hydrochloride | 880 | 865 |
| Phenylalanine sec-butyl ester hydrochloride | 850 | 841 |
| Phenylalanine tert.-butyl ester hydrochloride | 821 | 809 |
| Phenylalanine cyclohexyl ester hydrochloride | 807 | 799 |
| Phenylalanine amyl ester hydrochloride | 792 | 785 |
| Phenylalanine hexyl ester hydrochloride | 774 | 762 |
| Phenylalanine heptyl ester hydrochloride | 772 | 760 |
| Phenylalanine octyl ester hydrochloride | 763 | 740 |
| Phenylalanine nonyl ester hydrochloride | 751 | 729 |
| Phenylalanine decyl ester hydrochloride | 748 | 715 |
| Phenylalanine benzyl ester hydrochloride | 729 | 699 |
| Phenylalanine p-nitrophenyl ester | 703 | 689 |
| Pnenylalanine phenyl ester | 699 | 678 |

EXAMPLE 2

Cells of the microorganisms, grown and washed in a manner similar to example 1 and shown in table 4, were added to Reaction Solution B shown in Table 3 to equal 5 g/dl (final condition, pH 5.4, 5 ml), and kept at 37° C. for 16 hours. The resulting aspartyl-phenylalanine isopropyl ester was determined with an amino acid analyzer to give the results in Table 4.

TABLE 3

| Reaction Solution B* | |
|---|---|
| L-aspartic acid | 10 g/dl |
| L-phenylalanine isopropyl ester hydrochloride | 15 g/dl |

*The substrates are included in 0.1 M phosphoric acid buffers (final pH 5.4).

TABLE 4

| Microorganisms | | Aspartyl-phenylalanine isopropyl ester formed in Reaction Solution (mg/dl) |
|---|---|---|
| Corynebacterium sp. | ATCC 21251 | 862 |
| Corynebacterium xerosis | ATCC 373 | 324 |
| Candida intermedia | FERM-BP508 | 425 |
| Cryptococcus neoformans | IFO 4289 | 189 |
| Escherichia coli | FERM-BP477 | 1172 |
| Flavobcterium sewanens | FERM-BP476 | 1050 |
| Geotrichum candidum | IFO 4599 | 204 |
| Micrococcus luteus | ATCC 4698 | 915 |
| Pachysolen tannophilus | IFO 1007 | 148 |
| Trichosporon capitatum | IFO 1197 | 163 |
| Xanthomonas campestris | FERM-BP507 | 372 |
| Kluyveromyces thermotolerans | IFO 0662 | 135 |
| Endomyces ovetencis | IFO 1201 | 399 |
| Saccharomyces cerevisiae | IFO 2003 | 127 |
| Arthrobacter citreus | ATCC 11624 | 1018 |
| Cellulomonas flavigena | ATCC 8183 | 795 |
| Brevibacterium linens | ATCC 8377 | 939 |

EXAMPLE 3

Into 100 ml of Reaction Solution B was introduced 5 g of *Flavobacterium sewanens* FERM-BP476, grown and washed in a manner similar to Example 1, and the reaction was carried out at 37° C. for 24 hours.

The resulting reaction solution was spotted on a TLC plate for development in the form of a belt, and developed with a solvent system consisting of n-butanol: acetic acid: water=2:1:1. Part of the product aspartyl phenylalanine isopropyl ester was taken out and extracted with distilled water. Then, the resulting reaction product was crystallized to obtain 1023 mg of crystals. The obtained crystals were characterized as to optical rotation, melting point, and specific rotatory power, and the product obtained from Reaction Soluton B was identical to an authentic aspartyl-phenylalanine isopropyl ester specimen.

EXAMPLE 4

Into 100 ml of Reaction Solution B was introduced 5 g of *Arthrobacter citreus* ATCC 11624, grown and washed in a manner similar to Example 1, and the reaction was carried out at 37° C. for 24 hours.

The resulting reaction solution was spotted on a TLC plate for development in the form of a belt, and developed with a solvent system consisting of n-butanol: acetic acid: water=2:1:1. Part of the product aspartyl-phenylalanine isopropyl ester was taken out and extracted with distilled water. Then, the resulting reaction product was crystallized to obtain 1005 mg of crystals. The obtained crystals were characterized as to optical rotation, melting point, and specific rotatory power, and the product obtained from Reaction Solution B was identical to an authentic aspartyl-phenylalanine isopropyl ester specimen.

EXAMPLE 5

Into the culture solution of *Escherichia coli* FERM-BP477, maintained at 30° C. for 12 hours in the same medium used in Example 1, was poured under sterile conditions 10 ml of aqueous solution (adjusted to pH 5.4) containing 5 g/dl of L-aspartic acid and 10 g/dl of L-phenylalanine isopropyl ester, and the cultivation was further continued for 120 hours after the solution was adjusted under sterile conditions to pH 5.4. It was maintained at a pH of 5.4 by adjustments at intervals of 2 hours during incubation.

The resulting product in this culture solution was determined with an amino-acid analyzer and 489 mg/dl of aspartyl-phenylalanine isopropyl ester was formed.

EXAMPLE 6

Into the culture solution of *Brevibacterium linens* ATCC 8377, maintained at 30° C. for 12 hours in the same medium used in Example 1, was poured under sterile conditions 10 ml of aqueous solution (adjusted to pH 5.4) containing 5 g/dl of L-aspartic acid and 10 g/dl of L-phenylalanine isopropyl ester, and the cultivation was further continued for 10 hours after the solution was adjusted under sterile conditions to pH 5.4. It was maintained at a pH of 5.4 by adjustments at intervals of 2 hours during incubation.

The resulting product in this culture solution was determined with an amino-acid analyzer and 479 mg/dl of aspartyl-phenylalanine isopropyl ester was formed.

EXAMPLE 7

*Flavobacterium sewanens* FERM-BP476, grown and washed in a manner similar to example 1, was added to Reaction Solution A (phenylalanine n-butyl ester was used as the phenylalanine ester) to equal 5 g/dl (final conditions, pH 5.4, 5 ml) and allowed to react at 37° C. for 16 hours.

One liter of resulting enzyme reaction solution was left still for 24 hours at 0° C. and 3 g of crystals which separated out were filtered. Part of the product was taken out and measured by high-speed liquid chromatography (column:silicon ODS; eluent:methanol-water) to show that the product contained 1.67 g of L-aspartyl-L-phenylalanine n-butyl ester. these crystals were added to a mixed solution consisting of 3.8 g of 35% hydrochloric acid, 1.0 g of methanol and 2.0 g of water and the solution was mixed continuously for 7 days at 15° C. The resulting product was characterized with an amino-acid analyzer, infrared spectrum, acid titration, hydrochloric acid titration with the result that 0.38 g of the product L-aspartyl-L-phenylalanine methyl ester hydrochloride were obtained. The yield of L-aspartyl-L-phenylalanine butyl ester is 23%.

EXAMPLE 8

*Arthrobacter citreus ATCC* 11624, grown and washed in a manner similar to example 1, was added to Reaction Solution A (phenylalanine n-butyl ester was used as the phenylalanine ester) to equal 5 g/dl (final conditions, pH 5.4, 5 ml) and allowed to react at 37° C. for 16 hours.

One liter of resulting enzyme reaction solution was left still for 24 hours at 0° C. and 3 g of crystals which separated out were filtered. Part of the product was taken out and measured by high-speed liquid chromatography (column: silicon ODS; eluent: methanol-water) to show that the product contained 1.65 g of L-aspartyl-L-phenylalanine n-butyl ester. These crystals were added to a solution containing 3.8 g of 35% hydrochloric acid, 1.0 g of methanol and 2.0 g of water and the solution was mixed continuously for 7 days at 15° C. The product was filtered and dried to obtain 0.39 g of dried white crystals. The resulting product was characterized with an amino-acid analyzer, infrared spectrum, acid titration, and hydrochloric-acid titration with the result that 0.36 g of the product L-aspartyl-L-phenylalanine methyl ester hydrochloride was obtained. The yield of L-aspartyl-L-phenylalanine butyl ester is 22%.

To determine if any other specific microorganism, which is a member of the previously specified genuses, is suitable for the purposes of this invention, one would follow the procedures outlined in the examples given above and analyze the resulting product as described above. A suitable microorganism is one which is capable of bringing about condensation of aspartic acid and PR.

Many modifications and variations of the present invention are possible in light of the above teachings. Therefore, it is to be understood that within the scope of the appended claims, the invention may be practiced otherwise than as specifically described.

What is claimed as new and desired to be secured by letters patents is:

1. A process for the production of a dipeptide ester, which comprises:
   contacting L-aspartic acid and an ester of L-phenylalanine with a microorganism, wherein the ester of L-phenylalanine comprises L-phenylalanine which is esterified with
   (a) a straight-chain, branched or cyclic alkyl group of 2 or more carbon atoms,
   (b) an aryl group of 5 or more carbon atoms which may be substituted with one or more halogens, an alkyl group of 1–10 carbon atoms, a nitro group, or a cyano group, or
   (c) an aralkyl group of 6 or more carbon atoms, wherein the microorganism is selected from the group consisting of:
   *Corynebacterium sp.*: ATCC 21251,
   *Corynebacterium xerosis*: ATCC373,
   *Candida intermedia*: FERM-BP508,
   *Cyptococcus neoformans*: IFO 4289,
   *Escherichia coli*: FERM-BP477,
   *Flavobacterium sewanens*: FERM-BP476,
   *Geotrichum candidum*: IFO 4599,
   *Micrococcus luteus*: ATCC 4698,
   *Pachysolen tannophilus*: IFO 1007,
   *Trichosporon capitatum*: IFO 1197,
   *Xanthomonas campestris*: FERM-BP507,
   *Kluyveromyces thermotolerans*: IFO 0662,
   *Endomyces ovetencis*: IFO 1201,
   *Saccharomyces cerevisiae*: IFO 2003,
   *Arthrobacter citreus*: ATCC 11624,
   *Cellulomonas flavigena*: ATCC 8183, and
   *Brevibacterium linens*: ATCC 8377.

2. The process of claim 1, wherein the ester of L-phenylalanine is associated with an acid in a salt form.

3. The process of claim 2, wherein the salt form is hydrochloride.

4. The process of claim 1, wherein the L-aspartic acid is associated with an acid in a salt form.

5. The process of claim 1 wherein the microorganism is cultured under aerobic conditions at pH 4–8 and at a temperature of 25° C.–40° C. for a time period in the range of 1–10 days.

6. The process of claim 1, wherein the microorganism is *Corynebacterium sp.* ATCC 21251.

7. The process of claim 1, wherein the microorganism is *Corynebacterium xerosis*.

8. The process of claim 1, wherein the microorganism is *Candida intermedia* FERM-BP508.

9. The process of claim 1, wherein the microorganism is *Cryptococcus neoformans* IFO 4289.

10. The process of claim 1, wherein the microorganism is *Escherichia coli.* FERM-BP477.

11. The process of claim 1, wherein the microorganism is *Flavobacterium sewanens* FERM-BP476.

12. The process of claim 1, wherein the microorganism is *Geotrichum candidum* IFO 4599.

13. The process of claim 1, wherein the microorganism is *Micrococcus luteus* ATCC 4698.

14. The process of claim 1, wherein the microorganism is *Pachysolen tannophilus* IFO 1007.

15. The process of claim 1, wherein the microorganism is *Trichosporon capitatum* IFO 1197.

16. The process of claim 1, wherein the microorganism is *Xanthomonas campestris* FERM-BP507.

17. The process of claim 1, wherein the microorganism is *Kluyveromyces thermotolerans* IFO 0662.

18. The process of claim 1, wherein the microorganism is *Endomyces ovetencis* IFO 1201.

19. The process of claim 1, wherein the microorganism is *Saccharomyces cerevisiae* IFO 2003.

20. The process of claim 1, wherein the microorganism is *Arthrobacter citreus* ATCC 11624.

21. The process of claim 1, wherein the microorganism is *Cellulomonas flavigena* ATCC 8183.

22. The process of claim 1, wherein the microorganism is *Brevibacterium linens* ATCC 8377.

* * * * *